(12) United States Patent
Smith et al.

(10) Patent No.: US 9,096,887 B2
(45) Date of Patent: *Aug. 4, 2015

(54) ANALYTICAL METHOD FOR FAB AND FAB' MOLECULES

(71) Applicant: UCB PHARMA, S.A., Brussels (BE)

(72) Inventors: Bryan John Smith, Slough (GB); Helen Marie Kirke, Slough (GB)

(73) Assignee: UCB PHARMA, S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,055

(22) Filed: May 12, 2014

(65) Prior Publication Data
US 2014/0242625 A1    Aug. 28, 2014

Related U.S. Application Data

(63) Continuation of application No. 13/812,692, filed as application No. PCT/GB2011/001135 on Jul. 28, 2011, now Pat. No. 8,722,353.

(51) Int. Cl.
*C12Q 1/37*    (2006.01)
*G01N 33/68*   (2006.01)

(52) U.S. Cl.
CPC .............. *C12Q 1/37* (2013.01); *G01N 33/6857* (2013.01); *G01N 2333/96433* (2013.01)

(58) Field of Classification Search
None
See application file for complete search history.

(56) References Cited

U.S. PATENT DOCUMENTS 8,722,353 B2 *   5/2014   Smith et al. ................. 435/23

FOREIGN PATENT DOCUMENTS

WO   WO 2005/059106   6/2005
WO   WO 2008/025528   3/2008

OTHER PUBLICATIONS

Huang, H. Z. et al. "Direct Identification and Quantification of Aspartyl Succinimide in an IgG2 mAb by RapiGest Assisted Digestion" *Analytical Chemistry*, Feb. 15, 2009, pp. 1686-1692, vol. 81, No. 4.
Yang, H. et al. "Mass spectrometric analysis of asparagine deamidation and aspartate isomerization in polypeptides" *Electrophoresis*, Jun. 1, 2010, pp. 1764-1772, vol. 31, No. 11.
Chelius, D. et al. "Identification and Characterization of Deamidation Dites in the Conserved Regions of Human Immunoglobulin Gamma Antibodies" *Analytical Chemistry*, Sep. 15, 2005, pp. 6004-6011, vol. 77, No. 18.
Kroon, D. et al. "Identification of Sites of Degradation in a Therapeutic Monoclonal Antibody by Peptide Mapping" *Pharmaceutical Research*, Nov. 1, 1992, pp. 1386-1393, vol. 9, No. 11.
Leong, S. et al. "Adapting pharmacokinetic properties of a humanized anti-interleukin-8 antibody for therapeutic applications using site-specific pegylation" *Cytokine*, Nov. 7, 2001, pp. 106-119, vol. 16, No. 3.
Written Opinion in International Application No. PCT/GB2011/001135, Jan. 3, 2012, pp. 1-7.
Teshima, G. "Deamidation in Proteins and Peptides" IonSource.com, Nov. 21, 2000, pp. 1-8, XP002665740.

\* cited by examiner

*Primary Examiner* — Ralph Gitomer
(74) *Attorney, Agent, or Firm* — Saliwanchik, Lloyd & Eisenschenk (57) ABSTRACT

A method of measuring acidic species generated by degradation of a Fab or Fab' component of a Fab-PEG or a Fab'-PEG is provided. The method involves: a) cleaving PEG and a linker from the Fab-PEG or Fab'-PEG with an enzyme; b) optionally separating the PEG and linker from the Fab or Fab' to provide isolated Fab or Fab'; and c) quantitatively analyzing acidic species associated with the cleaved Fab or Fab' and/or the cleaved PEG.

12 Claims, 11 Drawing Sheets

Figure 1 Schematic diagram of a PEGylated Fab' format.

Figure 2 Schematic diagram of a PEGylated Fab' format with deamidation in the Fab' fragment Figure 3 Schematic diagram of a PEGylated Fab' format with deamidation in the Fab' fragment and hydrolysis of the linker to generate acidic species Figure 4 Schematic representation of the hydrolysis of Fab' and PEG maleimide followed by ring opening of the PEG linker succinimide ring Figure 5
Analysis of combined acidic species, linker hydrolysis generated acidic species and acidic species generated through deamidation

Figure 6

Figure 7 Efficiency of Tryptic Digest Conditions followed by HTRP HPLC

Figure 8 Fab' PEG CEX HPLC digest profile

Figure 9 cIEF profile of tryptic digest of Fab' PEG

Figure 10

SEQ ID NO: 1 shows the amino acid sequence of CDRH1 of CDP870.
Asp Tyr Gly Met Asn SEQ ID NO: 2 shows the amino acid sequence of CDRH2 of CDP870
Trp Ile Asn Thr Tyr Ile Gly Glu Pro Ile Tyr Ala Asp Ser Val Lys Gly SEQ ID NO: 3 shows the amino acid sequence of CDRH3 of CDP870.
Gly Tyr Arg Ser Tyr Ala Met Asp Tyr SEQ ID NO: 4 shows the amino acid sequence of CDRL1 of CDP870.
Lys Ala Ser Gln Asn Val Gly Thr Asn Val Ala SEQ ID NO: 5 shows the amino acid sequence of CDRL2 of CDP870.
Ser Ala Ser Phe Leu Tyr Ser SEQ ID NO: 6 shows the amino acid sequence of CDRL3 of CDP870.
Gln Gln Tyr Asn Ile Tyr Pro Leu Thr SEQ ID NO: 7 shows the amino acid sequence of the light chain variable region CDP870
Asp Ile Gln Met Thr Gln Ser Pro Ser Ser Leu Ser Ala Ser Val Gly Asp Arg Val Thr Ile Thr
Cys Lys Ala Ser Gln Asn Val Gly Thr Asn Val Ala Trp Tyr Gln Gln Lys Pro Gly Lys Ala
Pro Lys Ala Leu Ile Tyr Ser Ala Ser Phe Leu Tyr Ser Gly Val Pro Tyr Arg Phe Ser Gly Ser
Gly Ser Gly Thr Asp Phe Thr Leu Thr Ile Ser Ser Leu Gln Pro Glu Asp Phe Ala Thr Tyr Tyr
Cys Gln Gln Tyr Asn Ile Tyr Pro Leu Thr Phe Gly Gln Gly Thr Lys Val Glu Ile Lys SEQ ID NO:8 shows the amino acid sequence of the heavy chain variable region CDP870.
Glu Val Gln Leu Val Glu Ser Gly Gly Gly Leu Val Gln Pro Gly Gly Ser Leu Arg Leu Ser
Cys Ala Ala Ser Gly Tyr Val Phe Thr Asp Tyr Gly Met Asn Trp Val Arg Gln Ala Pro Gly
Lys Gly Leu Glu Trp Met Gly Trp Ile Asn Thr Tyr Ile Gly Glu Pro Ile Tyr Ala Asp Ser Val
Lys Gly Arg Phe Thr Phe Ser Leu Asp Thr Ser Lys Ser Thr Ala Tyr Leu Gln Met Asn Ser
Leu Arg Ala Glu Asp Thr Ala Val Tyr Tyr Cys Ala Arg Gly Tyr Arg Ser Tyr Ala Met Asp
Tyr Trp Gly Gln Gly Thr Leu Val Thr Val Ser Ser

Figure 11

SEQ ID NO: 9 shows the amino acid sequence of a grafted anti-TNFα Fab CDP870 light chain.
Asp Ile Gln Met Thr Gln Ser Pro Ser Ser Leu Ser Ala Ser Val Gly Asp Arg Val Thr Ile Thr
Cys Lys Ala Ser Gln Asn Val Gly Thr Asn Val Ala Trp Tyr Gln Gln Lys Pro Gly Lys Ala
Pro Lys Ala Leu Ile Tyr Ser Ala Ser Phe Leu Tyr Ser Gly Val Pro Tyr Arg Phe Ser Gly Ser
Gly Ser Gly Thr Asp Phe Thr Leu Thr Ile Ser Ser Leu Gln Pro Glu Asp Phe Ala Thr Tyr Tyr
Cys Gln Gln Tyr Asn Ile Tyr Pro Leu Thr Phe Gly Gln Gly Thr Lys Val Glu Ile Lys Arg Thr
Val Ala Ala Pro Ser Val Phe Ile Phe Pro Pro Ser Asp Glu Gln Leu Lys Ser Gly Thr Ala Ser
Val Val Cys Leu Leu Asn Asn Phe Tyr Pro Arg Glu Ala Lys Val Gln Trp Lys Val Asp Asn
Ala Leu Gln Ser Gly Asn Ser Gln Glu Ser Val Thr Glu Gln Asp Ser Lys Asp Ser Thr Tyr Ser
Leu Ser Ser Thr Leu Thr Leu Ser Lys Ala Asp Tyr Glu Lys His Lys Val Tyr Ala Cys Glu Val
Thr His Gln Gly Leu Ser Ser Pro Val Thr Lys Ser Phe Asn Arg Gly Glu Cys SEQ ID NO: 10 shows the amino acid sequence of a grafted anti-TNFα Fab CDP870 heavy chain.
Glu Val Gln Leu Val Glu Ser Gly Gly Gly Leu Val Gln Pro Gly Gly Ser Leu Arg Leu Ser
Cys Ala Ala Ser Gly Tyr Val Phe Thr Asp Tyr Gly Met Asn Trp Val Arg Gln Ala Pro Gly
Lys Gly Leu Glu Trp Met Gly Trp Ile Asn Thr Tyr Ile Gly Glu Pro Ile Tyr Ala Asp Ser Val
Lys Gly Arg Phe Thr Phe Ser Leu Asp Thr Ser Lys Ser Thr Ala Tyr Leu Gln Met Asn Ser
Leu Arg Ala Glu Asp Thr Ala Val Tyr Tyr Cys Ala Arg Gly Tyr Arg Ser Tyr Ala Met Asp
Tyr Trp Gly Gln Gly Thr Leu Val Thr Val Ser Ser Ala Ser Thr Lys Gly Pro Ser Val Phe Pro
Leu Ala Pro Ser Ser Lys Ser Thr Ser Gly Gly Thr Ala Ala Leu Gly Cys Leu Val Lys Asp Tyr
Phe Pro Glu Pro Val Thr Val Ser Trp Asn Ser Gly Ala Leu Thr Ser Gly Val His Thr Phe Pro
Ala Val Leu Gln Ser Ser Gly Leu Tyr Ser Leu Ser Ser Val Val Thr Val Pro Ser Ser Ser Leu
Gly Thr Gln Thr Tyr Ile Cys Asn Val Asn His Lys Pro Ser Asn Thr Lys Val Asp Lys Lys Val
Glu Pro Lys Ser Cys Asp Lys Thr His Thr Cys Ala Ala

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial
<220> FEATURE:
<223> OTHER INFORMATION: Amino acid sequence of CDRH1 of CDP870

<400> SEQUENCE: 1

Asp Tyr Gly Met Asn
1               5

<210> SEQ ID NO 2
<211> LENGTH: 17
<212> TYPE: PRT
<213> ORGANISM: Artificial
<220> FEATURE:
<223> OTHER INFORMATION: Amino acid sequence of CDRH2 of CDP870

<400> SEQUENCE: 2

Trp Ile Asn Thr Tyr Ile Gly Glu Pro Ile Tyr Ala Asp Ser Val Lys
1               5                   10                  15

Gly

<210> SEQ ID NO 3
<211> LENGTH: 9
<212> TYPE: PRT
<213> ORGANISM: Artificial
<220> FEATURE:
<223> OTHER INFORMATION: Amino acid sequence of CDRH3 of CDP870

<400> SEQUENCE: 3

Gly Tyr Arg Ser Tyr Ala Met Asp Tyr
1               5
```

```
<210> SEQ ID NO 4
<211> LENGTH: 11
<212> TYPE: PRT
<213> ORGANISM: Artificial
<220> FEATURE:
<223> OTHER INFORMATION: Amino acid sequence of CDRL1 of CDP870

<400> SEQUENCE: 4

Lys Ala Ser Gln Asn Val Gly Thr Asn Val Ala
1               5                   10

<210> SEQ ID NO 5
<211> LENGTH: 7
<212> TYPE: PRT
<213> ORGANISM: Artificial
<220> FEATURE:
<223> OTHER INFORMATION: Amino acid sequence of CDRL2 of CDP870

<400> SEQUENCE: 5

Ser Ala Ser Phe Leu Tyr Ser
1               5

<210> SEQ ID NO 6
<211> LENGTH: 9
<212> TYPE: PRT
<213> ORGANISM: Artificial
<220> FEATURE:
<223> OTHER INFORMATION: Amino acid sequence of CDRL3 of CDP870

<400> SEQUENCE: 6

Gln Gln Tyr Asn Ile Tyr Pro Leu Thr
1               5

<210> SEQ ID NO 7
<211> LENGTH: 107
<212> TYPE: PRT
<213> ORGANISM: Artificial
<220> FEATURE:
<223> OTHER INFORMATION: Amino acid sequence of the light chain variable
      region of CDP870

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
                20                  25                  30

Val Ala Trp Tyr Gln Gln Lys Pro Gly Lys Ala Pro Lys Ala Leu Ile
            35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 8
<211> LENGTH: 118
<212> TYPE: PRT
<213> ORGANISM: Artificial
<220> FEATURE:
<223> OTHER INFORMATION: Amino acid sequence of the heavy chain variable
      region of CDP870
```

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 9
<211> LENGTH: 214
<212> TYPE: PRT
<213> ORGANISM: Artificial
<220> FEATURE:
<223> OTHER INFORMATION: Amino acid sequence of a grafted anti-TNF alpha
      Fab CDP870 light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

```
<210> SEQ ID NO 10
<211> LENGTH: 229
<212> TYPE: PRT
<213> ORGANISM: Artificial
<220> FEATURE:
<223> OTHER INFORMATION: Amino acid sequence of a grafted anti-TNF alpha
      Fab CDP870 heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225

<210> SEQ ID NO 11
<211> LENGTH: 10
<212> TYPE: PRT
<213> ORGANISM: Artificial
<220> FEATURE:
<223> OTHER INFORMATION: Subsequence of SEQ ID NO: 10, C-terminus Heavy
      Chain

<400> SEQUENCE: 11

Ser Cys Asp Lys Thr His Thr Cys Ala Ala
1               5                   10
```

ANALYTICAL METHOD FOR FAB AND FAB' MOLECULES

CROSS-REFERENCE TO RELATED APPLICATIONS

This application is a continuation of U.S. application Ser. No. 13/812,692, filed Apr. 3, 2013, now U.S. Pat. No. 8,722,353, which is the U.S. national stage application of International Patent Application No. PCT/GB2011/001135, filed Jul. 28, 2011.

The Sequence Listing for this application is labeled "Seq-List-replace.txt" which was created on Apr. 30, 2015 and is 8 KB. The entire contents of the sequence listing is incorporated herein by reference in its entirety.

The present invention relates to an improved assay method for measuring acidic species in PEGylated proteins. In particular, the present invention relates to an improved assay method for measuring acidic species for PEGylated Fab and PEGylated Fab' antibody formats.

PEGylated Fab and PEGylated Fab' antibody formats are useful in that they provide a circulating half-life in vivo similar to that of a whole antibody without the effector functions associated with a whole antibody. These formats have become useful in therapy and long term stability testing is required to support the regulatory approval process which licenses the sale of these therapeutic products. Furthermore, once approved for use by the general public manufactured product must be batch release tested before it can be made available for sale.

The presence of acidic species in the formulations, for example after storage may be indicative of degradation (in particular deamidation) of the Fab or Fab'. Deamidation is classed by regulatory authorities as a degradation route and as such limits for the levels of deamidation are set for the product. These levels should not be exceeded during the shelf-life of the product. Whilst not wishing to be bound by theory it is thought that asparagine residues may be degraded via a succinimide intermediate by deamidation to generate acidic species, such as isoaspartic acid/aspartic acid, as set out in Scheme 1:

R1 & R2 are a continuation of the Fab' sequence

This deamidation of asparagine residues may result in a change in the proteins overall charge and may increase immunogenicity of the Fab or Fab'. Additionally, this deamidation may result in changes in the function/efficacy of the Fab or Fab', which may lead to unpredictable therapeutic effects/side effects or simply loss of activity. This can increase the adverse effects in patients after administration of the formulation. Thus degradation must be minimised and storage times and conditions must be limited to those when little or no degradation occurs. Therefore, it is important to be able to measure the deamidation in a given PEGylated Fab or Fab' formulation. The analysis may impact on the shelf-life and storage conditions given on the product labelling. It is also important to be able to monitor the levels of deamidation in the product because if predefined limits are exceeded then this may result in marketed products being withdrawn from sale or a block on the release for sale of certain batches of the products. In theory deamidation in the protein could be measured by quantifying the acidic species generated therein.

At the present time the total acidic species content of PEGylated Fab or PEGylated Fab' is measured using Cation Exchange (CEX)-HPLC.

The method measures an aggregate or total value of acidic species in the product. However, there are a number of routes by which the acidic species are generated and not all of those are associated with the deamidation (and hence degradation) of the protein. Thus the value obtained from the analysis is not a value for the actual amount of deamidation in the protein. In fact it includes acidic species generated by:
degradation of the Fab' and
hydrolysis of the linker joining the Fab' or Fab and the PEG molecule.

Figure 3:
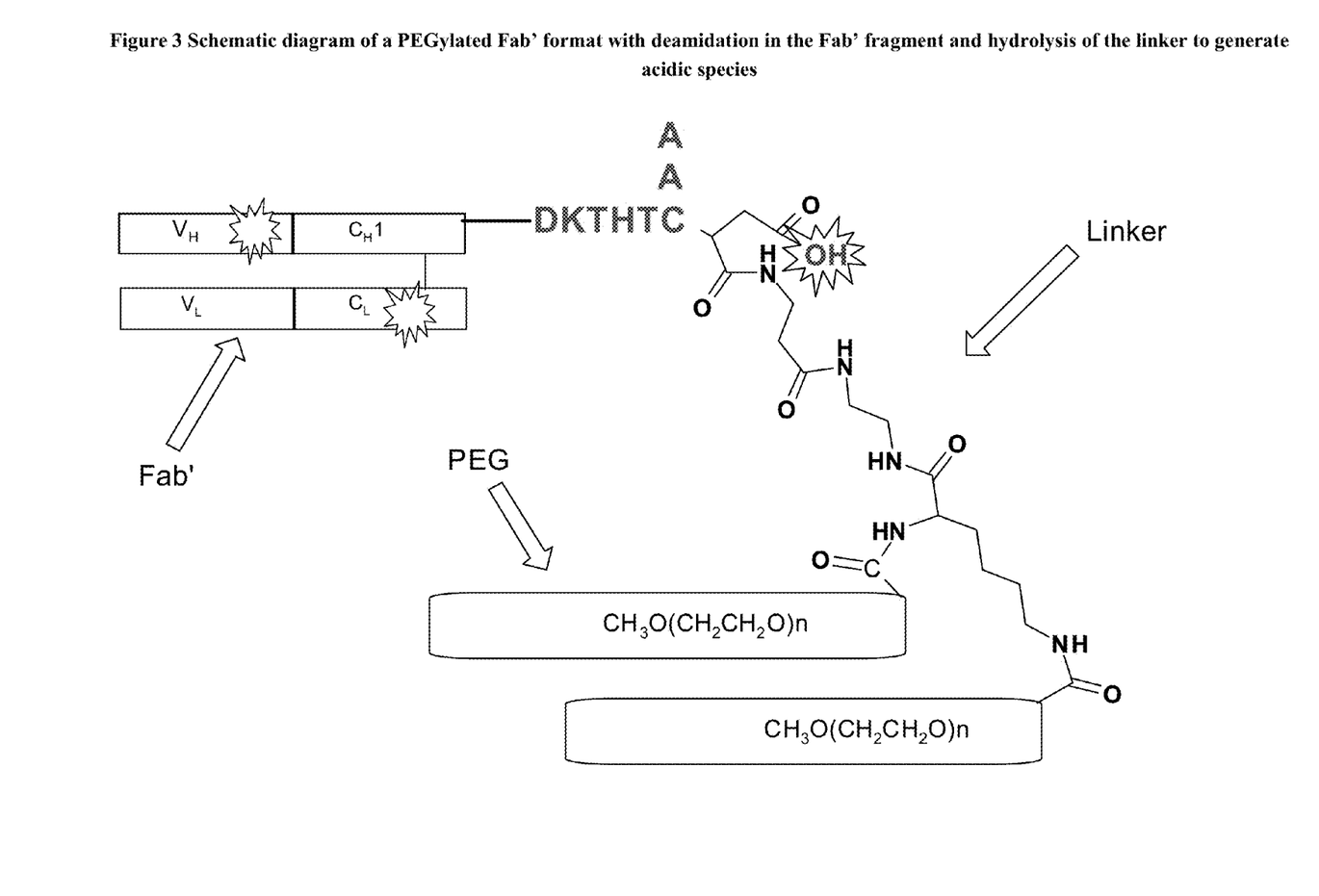
FIG. 3 shows a diagrammatic representation of deamidation and hydrolysis of the linker both of which generate acidic species.
Figure 4:
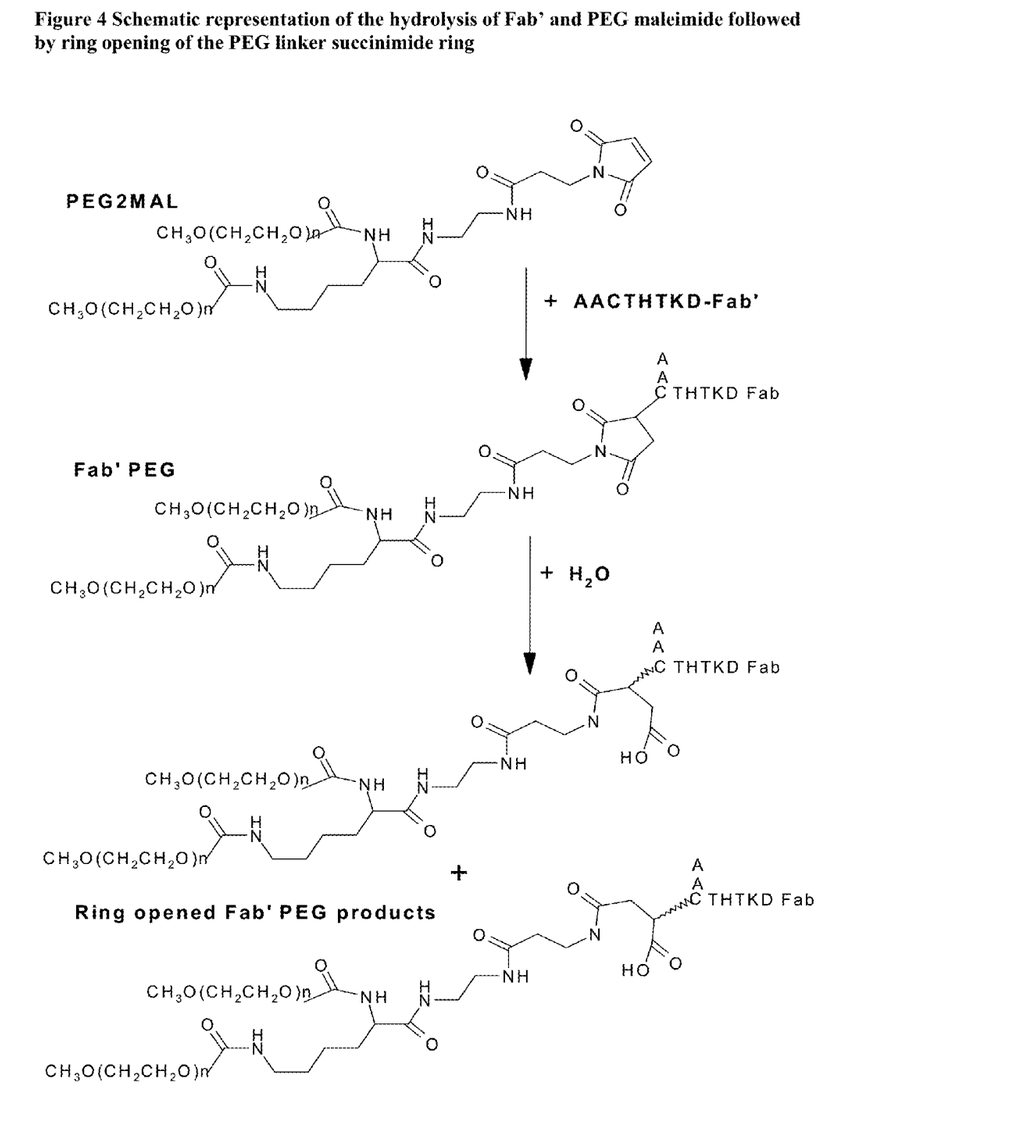
FIG. 4 shows a diagrammatic representation of the chemical process of PEGylation of a Fab' and subsequent ring opening to generate an acidic species.
Figure 5:
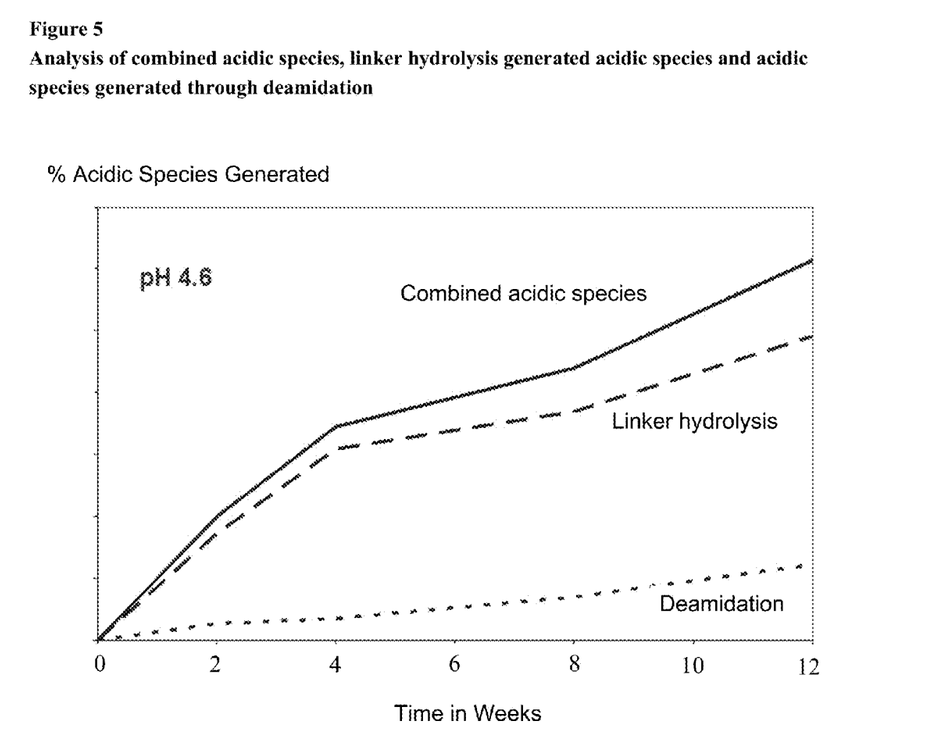
FIG. 5 is a diagrammatic representation of the relative proportions of acidic species values which contribute to the total acidic species content.
Figure 6:
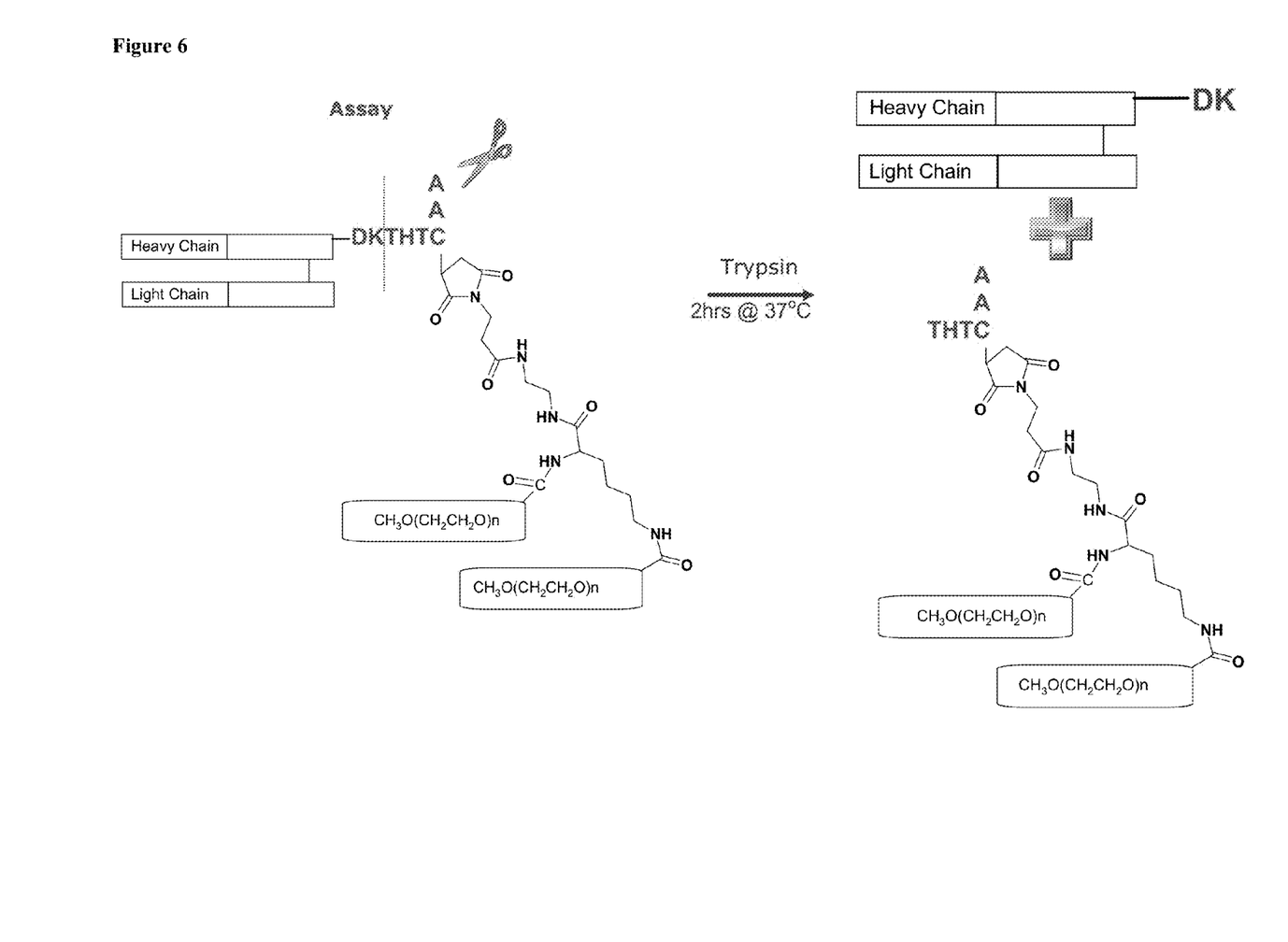
FIG. 6 is a diagrammatic representation of the species generated from a PEGylated Fab' after enzymatic digestion.

The hydrolysis of the PEG linker is thought to proceed through the succinimide ring as shown in FIG. 4. This hydrolysis may in fact be the dominant effect and generate a large component of the aggregate value of the acidic species when analysed. The total acidic species content is represented diagrammatically in FIG. 3, which shows acidic species generated in the protein by deamidation and acid species generated by hydrolysis of the linker. This can be represented diagrammatically as shown in FIG. 5, which shows the relative proportions of acidic species generated by hydrolysis of the linker by deamidation and a combination thereof.

The aggregate value of acidic species in a molecule is not of primary interest. Instead what is of interest is the amount of deamidation in the protein. However, the analysis of the total acidic species content does not provide a value representative of the deamidation in the protein.

Figure 1:
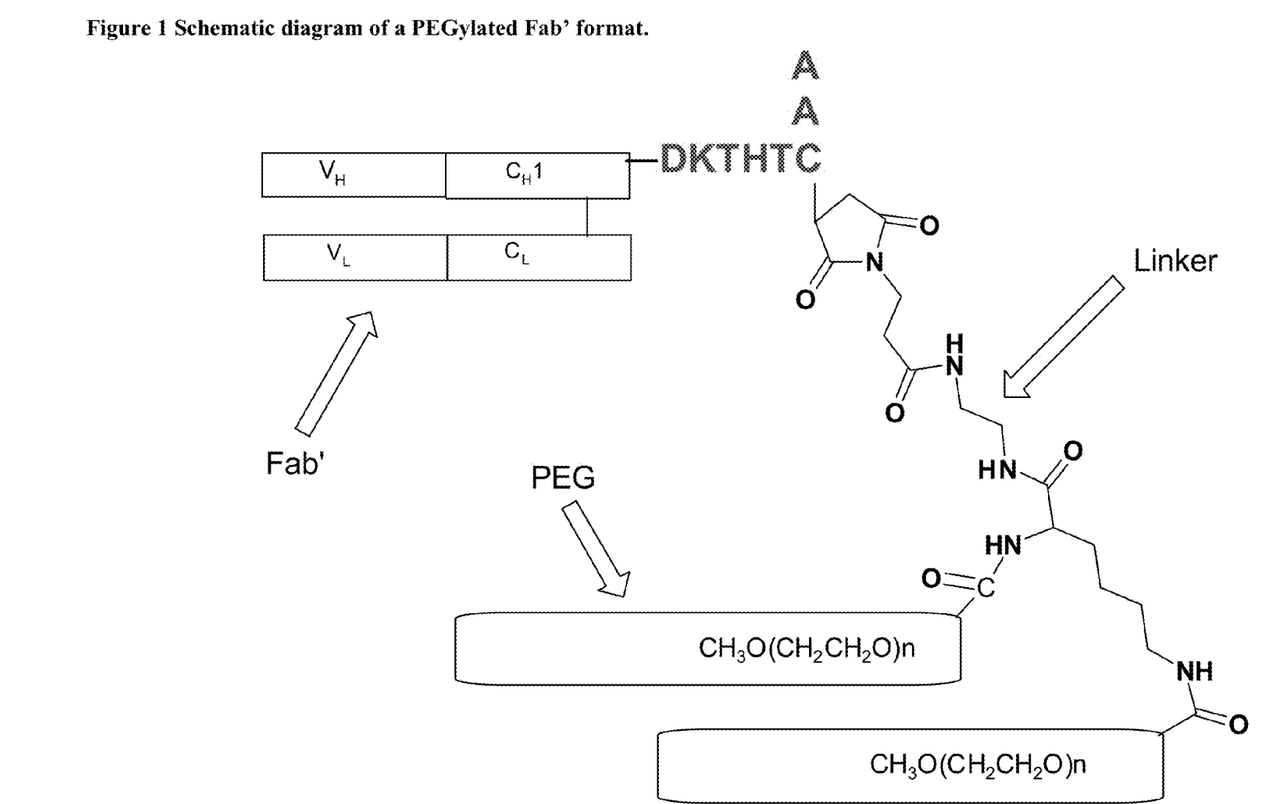
FIG. 1 shows a diagrammatic representation of a PEGylated Fab'.
Figure 2:
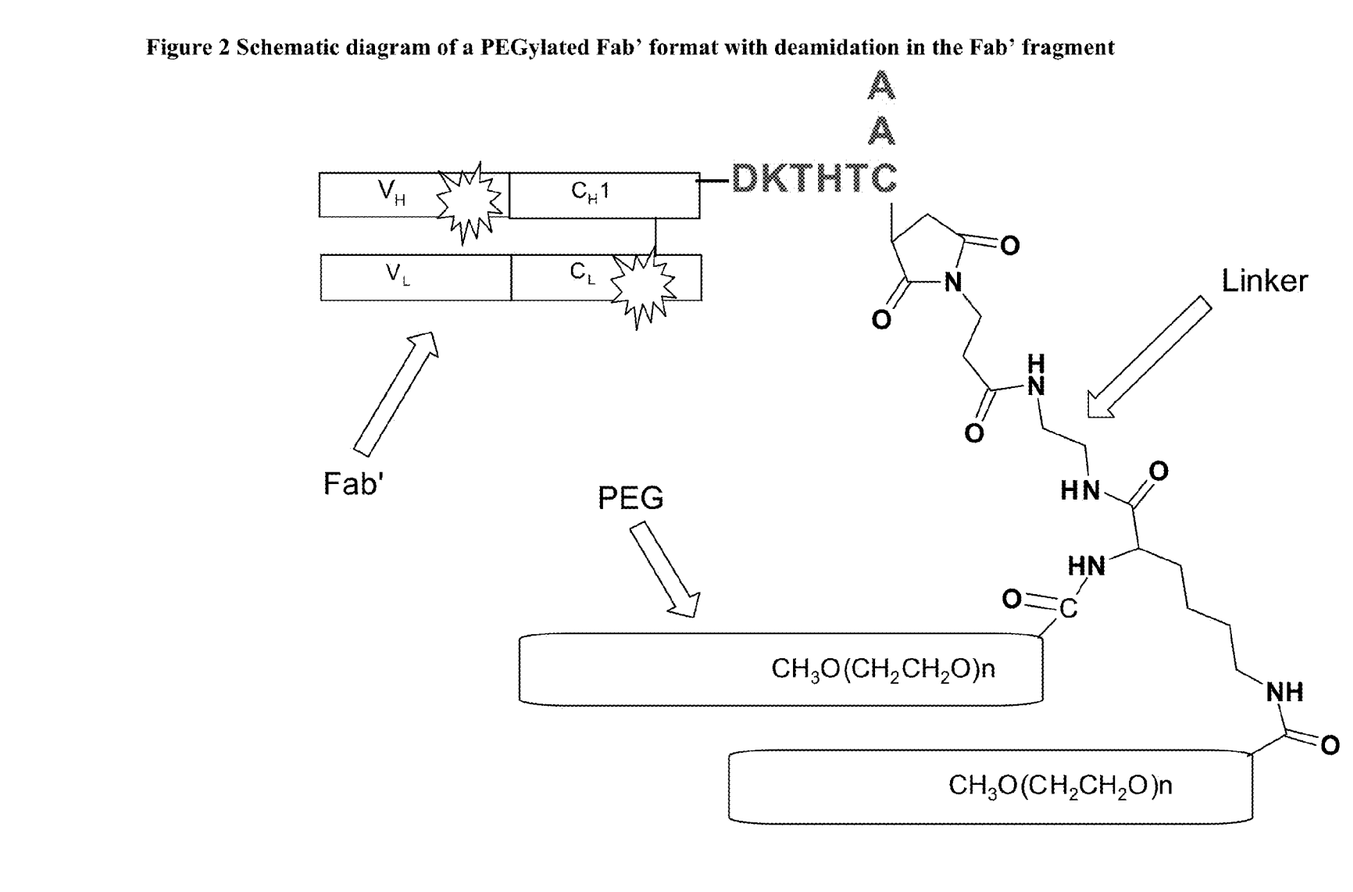
FIG. 2 shows a diagrammatic representation deamidation occurring in a PEGylated Fab'.

The amount of deamidation can be measured, for example employing ISOQUANT® aspartate detection kits. The deamidation is represented diagrammatically in FIG. 2, which shows the deamidation in the protein only. However, this deamidation assay is not particularly robust (Alfaro et al., Anal. Chem., 2008, 80, 3882-3889).

To support the commercial manufacture of a therapeutic product, robust analytical techniques are required. The inventors believe that they have designed a robust and effective method for the analysis of the deamidation of PEGylated proteins, in particular PEGylated Fabs and Fab's.

The method of the present disclosure allows the direct measurement of acidic species in the Fab or Fab' molecule resulting from deamidation/degradation in the Fab or Fab' molecule and not in the PEG or the linker.

Thus there is provided a method of measuring acidic species generated by degradation of a Fab or Fab' component of a Fab-PEG or a Fab'-PEG comprising the steps of:
  a) cleaving the PEG and linker from the Fab-PEG or Fab'-PEG with an enzyme,
  b) optionally separating the PEG and linker generated in step a) from the Fab or Fab', to provide a Fab or Fab' and
  c) quantitatively analyzing acidic species associated with the cleaved Fab or Fab' and/or the cleaved PEG.

By removing the PEG and linker from the Fab or Fab' the amount of deamidation in the protein can be measured by quantifying the acidic species therein. The method is reproducible and robust and furthermore the cleavage of the PEG and linker does not interfere with or change the amount of deamidation in the protein. Thus the deamidation in the cleaved Fab or Fab' should be representative of the deamidation in the protein portion of the PEGylated Fab or PEGylated Fab'.

In another embodiment the method also allows the extent of PEG linker hydrolysis to be determined by first determining the 'total' acidic species for the Fab-PEG or Fab'-PEG prior to cleavage in step (a) of the method and then subtracting the quantified acidic species associated with the Fab or Fab' component determined in step (c) of the method from the 'total' acidic species.

BRIEF DESCRIPTION OF THE FIGURES

FIG. 10 shows sequences 1 to 9.

FIG. 11 shows sequences 10 and 11.

BRIEF DESCRIPTION OF THE SEQUENCES

SEQ ID NO:1 shows the amino acid sequence of CDRH1 of CDP870.

SEQ ID NO:2 shows the amino acid sequence of CDRH2 of CDP870.

SEQ ID NO:3 shows the amino acid sequence of CDRH3 of CDP870.

SEQ ID NO:4 shows the amino acid sequence of CDRL1 of CDP870.

SEQ ID NO:5 shows the amino acid sequence of CDRL2 of CDP870.

SEQ ID NO:6 shows the amino acid sequence of CDRL3 of CDP870.

SEQ ID NO:7 shows the nucleotide and predicted amino acid sequence of the light chain variable region CDP870.

SEQ ID NO:8 shows the nucleotide and predicted amino acid sequence of the heavy chain variable region CDP870.

SEQ ID NO:9 shows the amino acid sequence of a grafted anti-TNFα Fab CDP870 light chain.

SEQ ID NO:10 shows the amino acid sequence of a grafted anti-TNFα Fab CDP870 heavy chain.

DETAILED DESCRIPTION OF THE INVENTION

Acidic species as employed herein is intended to refer to a moiety, molecule, comprising a carboxylic acid i.e. comprising the group —C(O)OH.

In one embodiment the enzyme is a protease, for example trypsin or chymotrypsin, such as trypsin. When the enzyme employed is trypsin then the cleavage point is expected to be between the K and T in, for example the sequence SCDKTHTCAA (SEQ ID NO:11) (C-terminus Heavy Chain) of the Fab' fragment. Advantageously cleavage at this point does not result in a change in the value of deamidation in the protein because the small portion of the hinge that is cleaved does not contain any asparagine residues.

Fab's naturally have a sequence in the hinge which is a suitable substrate for the enzyme. Fab molecules do not naturally have a substrate sequence for the enzyme but if desired an appropriate sequence can be engineered into an appropriate position allowing for removal of the PEG attached to the Fab by enzymatic digestion.

The enzymatic digestion may he performed at a temperature in the range 20 to 40° C. such as 25 to 38° C., in particularly it is optimally performed at 37° C.

In one embodiment when the starting entity is a PEGylated Fab' the enzyme cleaves the hinge portion of the Fab' and releases the PEG and linker from the Fab'.

The enzymatic digestion, for example tryptic digestion may be effected over a period of 30, 40, 50, 60, 70, 80, 90, 100, 110, 120, 130, 140, 150, 160 minutes or more.

The entities generated by digestion need not be separated because if a technique such as HPLC/cIEF is employed for the quantification of acidic species the entities generated have different retention times and thus can be quantified individually without an additional separation step.

However, optionally the entities generated by step a) may be separated by known techniques, for example cation exchange chromatography, cIEF, size exclusion chromatography and the like.

In one embodiment the acidic species associated with the Fab, Fab' and/or PEG is/are quantified.

In one embodiment the deamidation of the Fab or Fab' is measured.

In one embodiment acidic species in step c) are analysed employing HPLC analysis, for example employing an elution gradient. In one embodiment the HPLC analysis is CEX-HPLC analysis.

Alternatively, the amount of deamidation in the cleaved protein may be measured by capillary electrophoresis.

In one embodiment acidic species in step c) are analysed employing cIEF analysis, suitable cartridges include iCE280 available from Convergent Bioscience.

All publications, including but not limited to patents and patent applications cited in this specification are herein incorporated by reference as if each individual publication were specifically and individually indicated to be incorporated by reference herein as though fully set forth.

In a preferred embodiment the antibody is an anti-TNF antibody, more preferably an anti-TNF Fab' CDP870, as described in WO01/094585 (the contents of which are incorporated herein by reference).

In a one embodiment the antibody having specificity for human TNFα, comprises a heavy chain wherein the variable domain comprises a CDR having the sequence shown in SEQ ID NO:1 for CDRH1, the sequence shown in SEQ ID NO:2 for CDRH2 or the sequence shown in SEQ ID NO:3 for CDRH3.

In one embodiment the antibody comprises a light chain wherein the variable domain comprises a CDR having the sequence shown in SEQ ID NO:4 for CDRL1, the sequence shown in SEQ ID NO:5 for CDRL2 or the sequence shown in SEQ ID NO:6 for CDRL3.

In one embodiment the antibody comprises a heavy chain wherein the variable domain comprises a CDR having the sequence shown in SEQ ID NO:1 for CDRH1, the sequence shown in SEQ ID NO:2 for CDRH2 or the sequence shown in SEQ ID NO:3 for CDRH3 and a light chain wherein the variable domain comprises a CDR having the sequence shown in SEQ ID NO:4 for CDRL1, the sequence shown in SEQ ID NO:5 for CDRL2 or the sequence shown in SEQ ID NO:6 for CDRL3.

In one embodiment the antibody comprises SEQ ID NO:1 for CDRH1, SEQ ID NO: 2 for CDRH2, SEQ ID NO:3 for CDRH3, SEQ ID NO:4 for CDRL1, SEQ ID NO:5 for CDRL2 and SEQ ID NO:6 for CDRL3.

The antibody is preferably a CDR-grafted antibody molecule and typically the variable domain comprises human acceptor framework regions and non-human donor CDRs.

Preferably, the antibody comprises the light chain variable domain CDP870 (SEQ ID NO:7) and the heavy chain variable domain CDP870 (SEQ ID NO:8).

It is preferred that the antibody is a modified Fab fragment wherein the modification is the addition to the C-terminal end of its heavy chain one or more amino acids to allow the attachment of an effector or reporter molecule. Preferably, the additional amino acids form a modified hinge region containing one or two cysteine residue to which the effector or reporter molecule may be attached. Such a modified Fab fragment preferably has a heavy chain comprising or consisting of the sequence given as SEQ ID NO:10 and the light chain comprising or consisting of the sequence given as SEQ ID NO:9.

The present disclosure explicitly discloses embodiment comprising certain combinations of integers. The present disclosure also extends to embodiments consisting or consisting essentially of the said combinations of integers.

Preferences and/or embodiments may be combined as technically feasible.

The invention will now be described with reference to the following examples, which are merely illustrative and should not in any way be construed as limiting the scope of the present invention.

EXAMPLE

Tryptic Digestion Method

To an eppendorf, 1.0 mg Fab' PEG is added to 50mM NaOAc, 125mM NaCl pH 5.0 to 50 μL total volume. 50 μL 0.2M $Na_2HPO_4$ is added, followed by 40 μL trypsin resuspension buffer (50 mM Acetic Acid), the final pH should be in the region of pH 7.5. Vortex for 10 seconds.

The reaction is incubated at 37° C. for 2 hours. Analyse by CEX HPLC or imaged capillary isoelectrophoresis.

Digest Efficiency Determined by HTRP HPLC

Figure 7:
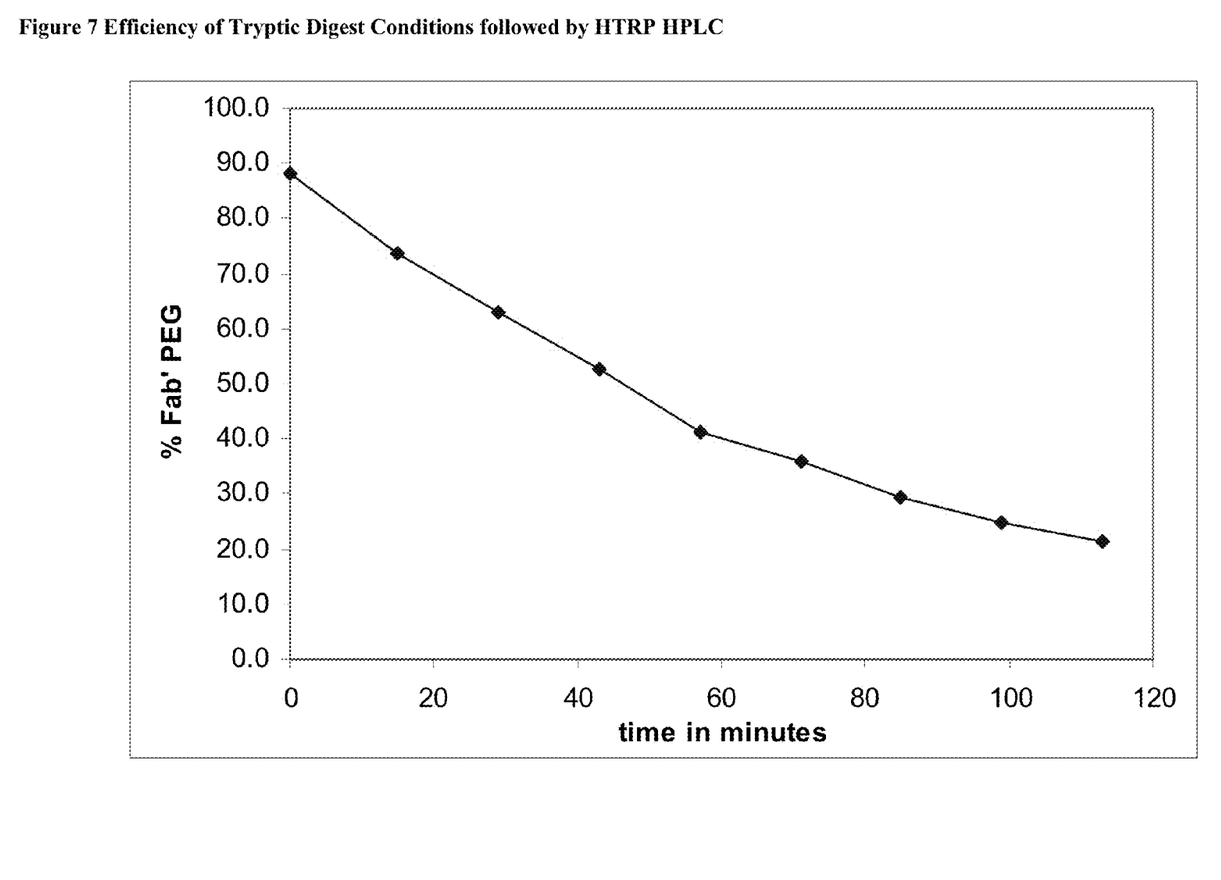
FIG. 7 shows efficiency of a trypsin digest of a PEGylated Fab' over time.

A tryptic digest using a Fab'PEG was set up using an Agilent 1100 series auto sampler incubated at 37° C., in order that the reaction could be injected directly onto HTRP HPLC assay. 9 injections of the Fab' Peg and Fab' control were carried out sequentially. Fab' PEG gave a digest profile shown in FIG. 7. This demonstrates that within two hours, the Fab' PEG product content is reduced to ~20%.

Analysis

Figure 8:
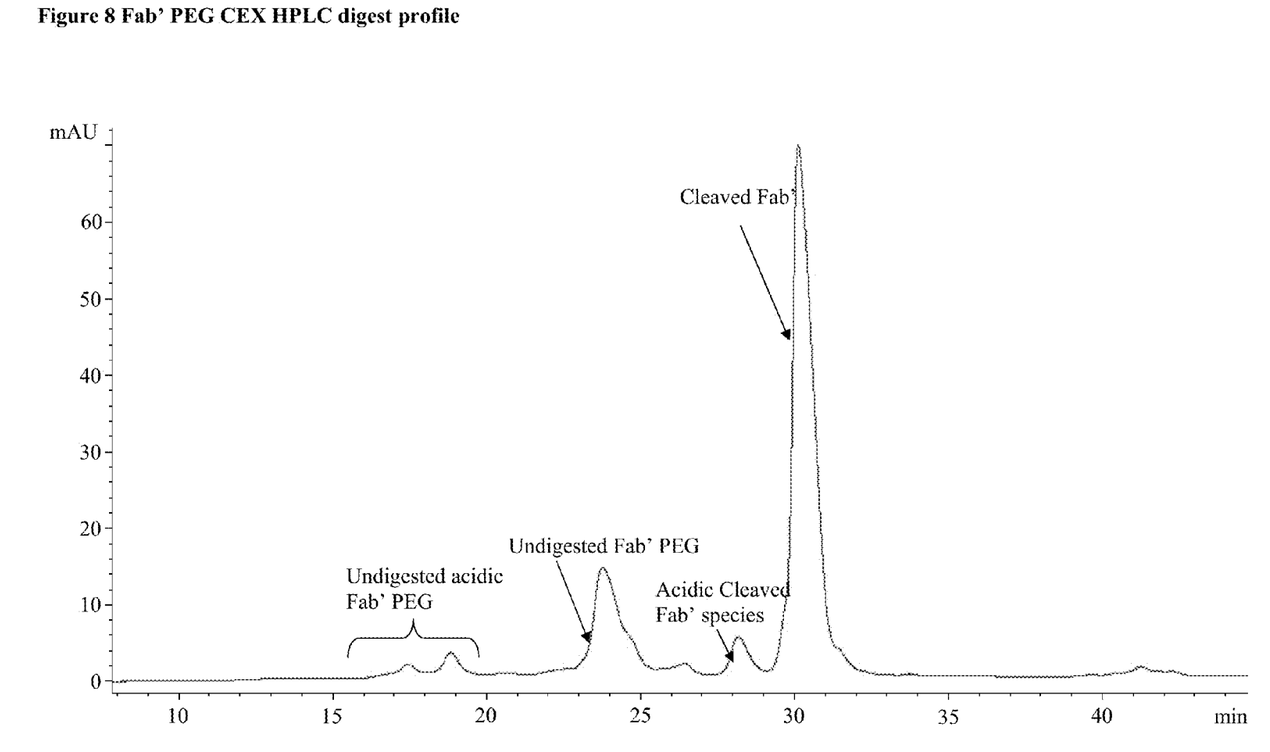
FIG. 8 is a CEX-HPLC analysis of the crude product resulting from trypsin digest of a PEGylated Fab'.

After digestion, samples were removed and diluted to 1 mg/mL in sample dilution buffer (20 mM Sodium Acetate pH 4.5). The Fab' PEG and cleaved Fab' can be identified along with their respective acidic species without pre-processing of the mixture obtained from the digestion step, as shown in FIG. 8. The following as shown in FIG. 8 are eluted sequentially; undigested acidic Fab' PEG species, undigested Fab' PEG, acidic cleaved Fab' species and cleaved Fab'.

Suitable Chromatographic Conditions for the Detection of Cleaved Fab' Acidic species by CEX HPLC

| | |
|---|---|
| Solvent A | equilibration buffer 10 mM 2-(N-morpholino)Ethane Sulfonic acid pH 6.2 |
| Solvent B | elution buffer 10 mM 2-(N-morpholino)Ethane Sulfonic acid, 50 mM sodium chloride pH 6.2 |
| Column | Dionex Propac SCX-10 column |
| Flow Rate | 0.5 mL/min |
| Stop Time | 75 min |
| Max Pressure | 250 bar |
| Method Run Pressure (guide) | ~60 bar |
| Column Temperature | 25° C. |
| Injection Volume | 100 μL |
| Autosampler Temperature | 4° C. |
| Detection Wavelength | 280 nm (16 bandwidth), 4 nm slit width |
| Loading | 100 μL at 1 mg/mL |

| Time | Solvent A (%) | Solvent B (%) | Flow Rate (mL/min) |
|---|---|---|---|
| 0.0 | 100 | 0 | 0.5 |
| 2.0 | 100 | 0 | 0.5 |
| 62.0 | 40 | 60 | 0.5 |
| 62.5 | 0 | 100 | 0.5 |
| 63.5 | 0 | 100 | 0.5 |
| 64.0 | 100 | 0 | 0.5 |
| 75.0 | 100 | 0 | 0.5 |

Data Analysis may be carried out using HP Chemstation software where the peaks are integrated, see FIG. 8 for an example of chromatogram of Fab' PEG digest using the suitable chromatographic conditions described. The following are detected; undigested acidic Fab' PEG, undigested Fab' PEG, acidic cleaved Fab', cleaved Fab'.

Alternative Method of Analysis Using Imaged Capillary Isoelectrophoresis

Sample Preparation for Analysis Using iCE280

A generic sample preparation of 200 µL volume is given below:

Tryptic Digest (desalted and free from any free ions at a concentration of 1 mg/ml)-40 ul (General rule: final concentration of the protein should be around 0.1-0.3 mg/ml in final sample mixture).

1% Methyl Cellulose: 70 µL (Methyl cellulose concentration in the final the mixture should be 0.35%).

Carrier Ampholytes: (3-10 Pharmalytes)-8 µL (Carrier ampholytes should have a concentration of 4% in the final sample mix).

pI markers: 1 µL each of two different pI markers are added whose pI values should lie on the either side of the protein and its related species.

HPLC grade water: Add required amount of HPLC water to make up the volume to 200 µL.

Mix the above sample by vortexing for 15-30 second to ensure proper mixing of different components. Spin the mixture at 16000 g for 10 minutes to remove air bubbles and dust particles, which would interfere with the analysis.

Instrument Settings and Analysis Employing iCE280 Technology iCE 280 from Convergent biosciences (Isogen in Europe) is an imaged capillary isoelectrophoresis instrument, which is used to determine pIs of various protein samples and their related species.

High voltage is applied across the capillary using an anode and cathode, which are dipped, in small reservoirs containing catholyte ($OH^-$) and anolyte ($H^+$). Samples are prepared with carrier ampholytes and on application of high voltage the protein molecules migrate according to their respective pIs and finally focus at it. The anolyte may be prepared by adding calculated amount of phosphoric acid to give a final solution of 0.08 M phosphoric acid in 0.1% methyl cellulose. The catholyte may be prepared by adding 10.4 µl of 50% w/w NaOH solution to 2 ml of 0.1% methyl cellulose. Catholyte must be freshly prepared and should not be reused. Generally 2 ml is enough for a single fill of the reservoir.

Generally for all non-PEGylated samples, a focusing period of 5-6 minutes at 3000 v should be enough, but since different proteins have different charge distribution, the focusing time would also vary accordingly. In that case the settings need to be optimised by running two or three samples.

Figure 9:
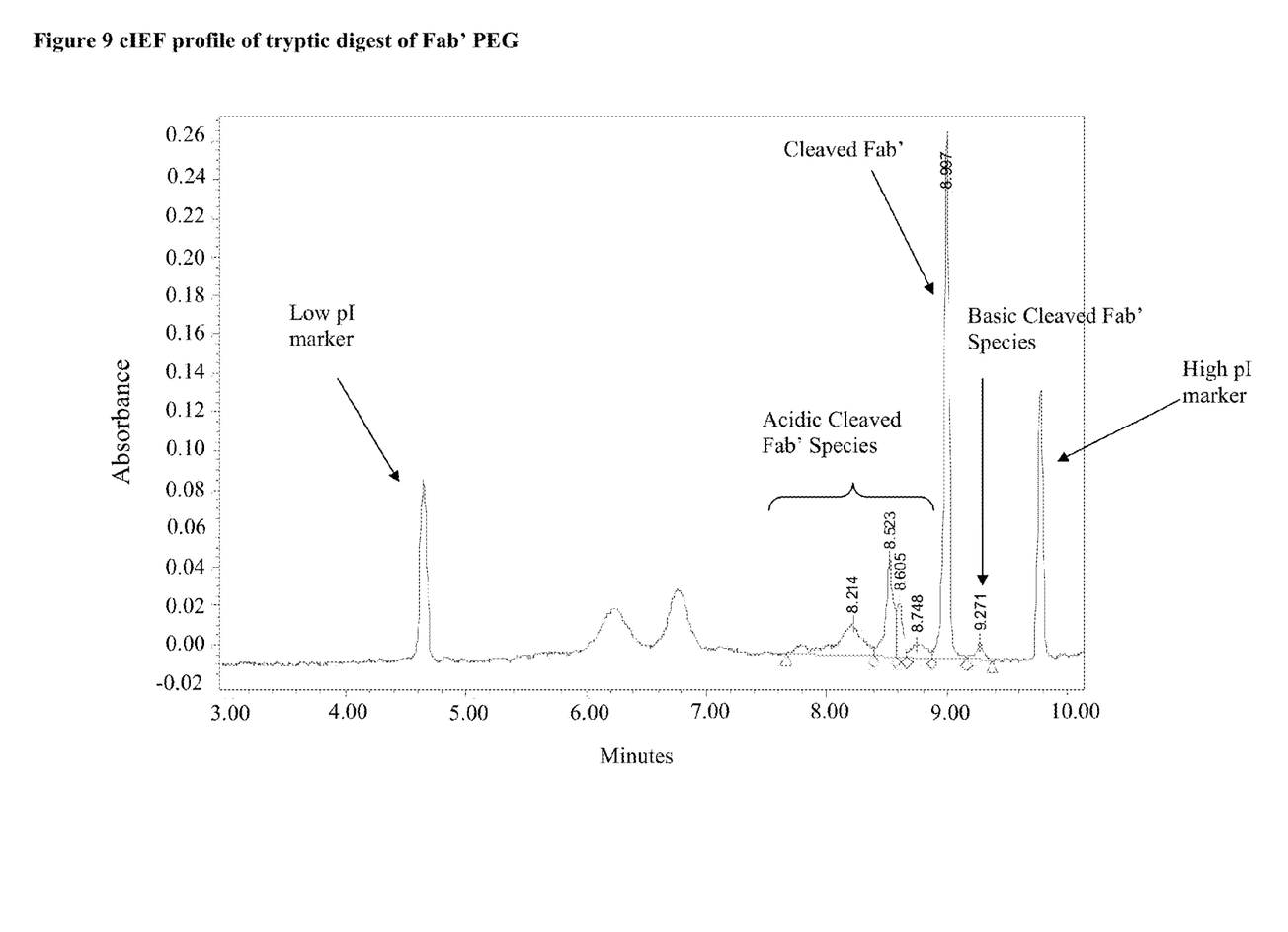
FIG. 9 is an iCEF of a PEGylated Fab' digested by trypsin.

Data analysis may be carried out using EZChrom software. Profiles can be compared by overlaying them using 'Supercompare' and electrophoregrams can be integrated using 'Method development' options within the EZChrom software. See FIG. 9 for an example of electrophoregram of Fab' PEG digest. The following are detected; low pI marker, acidic cleaved Fab' species, cleaved Fab' species, basic cleaved Fab' species, high pI marker.

The invention claimed is:

1. A method of quantitatively analyzing acidic species generated by degradation of a Fab or Fab' component of a Fab-PEG or a Fab'-PEG comprising the steps of:

a) cleaving the PEG and linker from the Fab-PEG or Fab'-PEG with an enzyme, b) optionally separating the PEG and linker generated in step a) from the Fab or Fab', to provide a Fab or Fab' and c) quantitatively analyzing acidic species associated with the cleaved Fab or Fab' and/or the cleaved PEG.

2. The method according to claim 1, wherein the enzyme is trypsin or chymotrypsin.

3. The method according to claim 1, wherein the cleaving in step a) is performed at a temperature in the range of 25° C. to 40° C.

4. The method according to claim 2, wherein step a) is performed at a temperature in the range of 25° C. to 40° C. with said enzyme.

5. The method according to claim 1, wherein the cleavage of step a) occurs between a lysine and a threonine in the C-terminal portion of the Fab or Fab' heavy chain.

6. The method according to claim 5, wherein the lysine and threonine are found in the sequence SCDKTHTCAA (SEQ ID NO: 11) located at the C-terminal of a Fab'.

7. The method according to claim 6, wherein the enzyme cleaves the hinge portion of the Fab' and releases the PEG and linker from the Fab'.

8. The method according to claim 1, wherein the PEG and linker generated in step a) is separated from the Fab or Fab' to provide a Fab or Fab'.

9. The method according to claim 8, wherein the separation is effected by cation exchange chromatography, cIEF, and/or size exclusion chromatography.

10. The method according to claim 1, wherein the acidic species is quantitatively analyzed by cation exchange chromatography or imaged capillary isoelectrophoresis.

11. The method according to claim 1, wherein said Fab' comprises SEQ ID NO: 9 and SEQ ID NO: 10.

12. The method according to claim 1, wherein said Fab' consists of SEQ ID NO: 9 and SEQ ID NO: 10.

* * * * *